United States Patent [19]
Strauss

[11] Patent Number: 5,993,790
[45] Date of Patent: Nov. 30, 1999

[54] NAIL EVULSION COMPOSITIONS AND METHOD FOR EVULSING NAILS AND TREATING NAIL AND NAIL BED INFECTIONS

[75] Inventor: Richard Strauss, Woodbury, N.Y.

[73] Assignee: Pedinol Pharmacal Inc., Farmingdale, N.Y.

[21] Appl. No.: 09/301,253

[22] Filed: Apr. 28, 1999

Related U.S. Application Data

[63] Continuation-in-part of application No. 09/129,002, Aug. 4, 1998.
[60] Provisional application No. 60/062,011, Aug. 4, 1997.
[51] Int. Cl.⁶ .............................. A61K 7/04; A61K 31/74; A61K 7/00; A61K 9/14
[52] U.S. Cl. ...................... 424/61; 424/78.02; 424/78.07; 424/401; 424/487; 514/858
[58] Field of Search ................... 424/61, 78.02, 424/78.07, 401, 487; 514/858

[56] References Cited

U.S. PATENT DOCUMENTS

| | | | |
|---|---|---|---|
| 5,120,529 | 6/1992 | Koch et al. | 424/61 |
| 5,346,692 | 9/1994 | Wohlrab et al. | 424/61 |

*Primary Examiner*—Shelley A. Dodson
*Assistant Examiner*—Marina Lamm
*Attorney, Agent, or Firm*—Darby & Darby

[57] ABSTRACT

Disclosed is a composition comprising a water based nail lacquer and urea, which is useful in the partial or complete evulsion of the nails, and in the treatment of fungal, yeast and bacterial infections of the nails and the nail beds. Also disclosed are methods for evulsing nails, and for treating antifungal and antibacterial infections, comprising the administration of the composition of the invention to the toenails or fingernails of a mammal.

20 Claims, No Drawings

NAIL EVULSION COMPOSITIONS AND METHOD FOR EVULSING NAILS AND TREATING NAIL AND NAIL BED INFECTIONS

This application is a continuation-in-part of application Ser. No. 09/129,002, filed Aug. 4, 1998, still pending, which is hereby incorporated by reference, which claims priority under 35 U.S.C. §119(e) of provisional application Ser. No. 60/062,011, filed Aug. 4, 1997, which is hereby incorporated by reference.

FIELD OF THE INVENTION

This invention relates to water based nail lacquer compositions, and methods for evulsing toenails or fingernails involving the topical administration of the composition. The invention also relates to methods for treating infected toenails and fingernails.

BACKGROUND OF THE INVENTION

Fungal infections associated with the nails of the hands and feet are difficult to treat, particularly in the later stages of the disease. Infections associated with the nails of the feet and hands include onychomycosis, the fungal infection tinea pedis (athlete's foot), and the bacterial infection paronychia, a superficial infection of the skin caused by staphylococci and yeast. However, particularly difficult to treat is onychomycosis.

Onychomycosis is a fungal infection which can spread beneath and over the fingernails and toenails and the nail beds located under the nails. Nails infected with onychomycosis often become thickened and lusterless with debris accumulating beneath the free edge of the nail. Onychomycosis and similar infections have become more common and more intractable in recent years particularly in immunosuppressed patients, such as patients infected with Human Immunodeficiency Virus (HIV) or patients suffering from Acquired Immunodeficiency Syndrome (AIDS).

Even in otherwise healthy patients, onychomycosis is difficult to treat, particularly in its later stages. For example, most skin infections and dermatological conditions respond very well to topical antifungal preparations such as the imidazole derivatives (miconazole, clotrimazole, enconazole, ketoconazole) described in U.S. Pat. No. 3,717,655, as useful for the topical treatment of fungal infections. Other topical treatments, such as ciclopirox olamine cream and naftifine hydrochloride cream, have also proven somewhat effective against some fungal and bacterial infections. However, for many forms of onychomycosis, such as those caused by *Trichophyton rubrum, T schoenleinni, T. mentagrophytes, T. sulfureum, T. verrucossum, T. interdigitalis, Epidermophyton floccosum, Microsporum audouinii, M. canis*, or *M. gypseum* and various forms of pedis, most topical antifungal preparations have proven to be ineffective.

For deep-seated onychomycosis and pedis that have spread uncontrolled beneath the nail beds, systemic therapy is often required. One common method of systemic therapy is the administration of griseofulvin, an oral antifungal agent. However, griseofulvin has undesirable side effects such as headaches, gastrointestinal distress, photosensitivity, rashes, or leukopenia. There has been some demonstrated success utilizing topical imidazole in conjunction with oral griseofulvin to increase the cure rate, but even with simultaneous topical and systemic treatment, there are unwanted side effects associated with administration of oral antifungal agents such as griseofulvin.

In addition to causing irritation, onychomycosis and similar conditions often create damage to the nails and nail beds causing the nails to thicken, discolor, and to crack and crumble around the edges. Thus even if the onychomycosis is treated, extensive repair of the damaged nail is often required.

Topical treatments for fungal infections are particularly advantageous over systemic therapy in that topical treatments avoid the negative side effects associated with systemic drugs. However, topical antibiotic or antifungal compositions, such as nail lacquers, are often ineffective because the antibiotics cannot penetrate through the nail to which it is applied in order to reach the infected nail beds. As a result, the prior art topical treatments do not effectively deliver the antimicrobial agent to the source of the fungus or bacteria.

Conventional cosmetic nail lacquers are generally polymer-based lacquers that use nitrocellulose as a film forming agent. Modifiers such as plasticizers and resins are generally required to keep the nitrocellulose from becoming too brittle and to increase the adherence of the nitrocellulose film to the surface of the nail. Most resins used today are synthetic resins such as methacrylate and polyvinyl acetate. A common plasticizer used with nitrocellulose is tricresyl phosphate.

Thus, polymer based lacquers with antimicrobial agents have not been successful in imparting antimicrobial and antiviral agents to the nails and nail beds because nitrocellulose polymers are water insoluble, and require the use of a solvent as a carrier medium. Common solvents include ethyl acetate, amyl acetate, butyl acetate, ethyl alcohol, butyl alcohol and acetone. Butyl alcohol is most commonly used with nitrocellulose lacquers. However, these solvents often adversely interfere with the antimicrobial and antiviral agents, rendering the agents ineffective in treating fingernail and toenail infections. Solvent based lacquers are also not satisfactory because they cause the nails to dry out and also leave a brittle surface. Also, polymer based lacquers are often very viscous, and the viscosity can interfere with the delivery of the antimicrobial agent to the source of the infection which is often embedded beneath the nail.

One method of enhancing the delivery of antimicrobial and antiviral agents to the nail beds, and thereby enhancing the effectiveness of the agents, is to evulse or remove the nails prior to treatment. Prior art methods of evulsing the nails include mechanical or surgical means. There are a number of drawbacks associated with the prior art methods of evulsion, including pain to the patient, and the increased costs and time of treatment associated with the physical removal of nails.

Applicants have now discovered an effective, water-based nail lacquer that partially or completely evulses the nails, thereby enhancing the delivery of antimicrobial and antiviral agents to the nail beds, and increasing the effectiveness of topical treatment with antiviral and antimicrobial agents.

The present invention comprises a method for treating damaged and infected nails with a topical, water based nail lacquer which is applied to the nail and surrounding tissues. The method leaves a strong and durable enamel over the nail, and partially or completely evulses the nail to allow topical medication to reach the source of the infection.

The compositions of the invention provide an improved method of evulsing nails. The composition of the invention further provides improved methods for delivering antimicrobial or antiviral agents to infected nails and nail beds.

SUMMARY OF THE INVENTION

The invention comprises in particular embodiments a composition comprising a water-based nail lacquer and urea, an evulsing agent.

The composition may comprise from about 85 to about 95% by weight of a water based nail lacquer; from about 0.5 to about 1.5% by weight of a preservative; from about 0.5 to about 10% by weight of urea; from about 1.0 to about 10% by weight of deionized water; and from about 0.1 to about 0.6% by weight of a natural additive.

In a preferred embodiment, the invention comprises from about 90 to about 95% by weight of a water based nail lacquer; from about 0.75 to about 1.25% by weight of a preservative; from about 1.0 to about 10.0% by weight urea; from about 3.0 to about 5.0% by weight deionized water; and from about 0.2 to about 0.5% by weight of a natural additive.

In a still more preferred embodiment, the invention comprises about 93.55% by weight of a water based nail lacquer; about 1.0% by weight of a preservative; about 1.25% by weight of urea; about 3.70% by weight deionized water; and about 0.5% by weight natural additives.

In separate embodiments, the invention may contain up to about 5% by weight of a keratolytic agent. Exemplary keratolytic agents include salicylic acid, acetic acid, glycolic acid, or combinations thereof.

The composition may also include up to about 4.0% by weight of a solvent, to aid in absorption. However, it should be noted that even with up to 4.0% by weight of a solvent, such as dimethyl sulfoxide (DMSO) or ethylacetate, the composition is water-based, since the major component of the composition is a water-based lacquer.

The invention is also directed to methods for partially or completely evulsing the fingernails or toenails of a mammal, comprising the topical application of the composition of the invention on or under the fingernails or toenails, or to the surrounding skin. The composition of the invention may be administered to the fingernails and toenails and surrounding areas by a variety of methods well known in the art, including by means of an applicator or dispenser, such as a brush, sponge, cloth, patch, dropper, tubular dispenser or spray.

In another embodiment, the invention is directed to a method for treating fungal infections of the toenails and fingernails, and infected nail beds, by treatment with the composition of the invention to cause partial or complete evulsion of the nails, and subsequent treatment with anti-bacterial or antifungal agents. Typical infections for which the invention is useful include onychomycosis and tinea pedis, and bacterial and yeast infections such as paronychia.

The nail lacquer can be safely applied to fingernails, toenails and skin and if necessary, over small cuts and abrasions near the area where the nails and skin meet. When applied to the surface of the infected nail, the nail lacquer of the invention is effective in evulsing the nail to allow improved delivery of an antifungal or antimicrobial agent to infected areas. The water based lacquer provides a superior delivery vehicle for the urea in comparison to organic, solvent-based lacquers. In addition, because the lacquer is water based and does not employ any solvents, the lacquer does not dry the tissues or leave them in a hard and brittle condition.

The present invention also comprises methods of treatment of damaged and infected fingernails, toenails and nail beds by topical application of the water-based topical nail lacquer of the invention to the surface of an infected nail. The method seals in the urea and forms a hardened enamel around the nail surface to allow easier nail evulsion. The water based nail lacquer used in the present invention also acts as an improved carrier of the urea agent, delivering it efficiently to the source of the fungal or bacterial infection. Because it is water based the nail enamel of the present invention is non-drying (i.e. it does not cause dehydration of the nail and the surrounding tissue), an advantage to the already damaged nail surface. Further, there are no ingredients in the nail enamel which interferes with the urea agent, unlike most organic solvent based nail lacquers.

DETAILED DESCRIPTION OF THE PREFERRED EMBODIMENTS

The nail lacquer of the present invention generally forms a clear and adherent enamel over the surface of fingernails and toenails and preferably employs no pigments.

A preferred agent for the water-based nail lacquer of the invention is urea, an evulsing agent, which may be present in the amount of about 0.5 to about 10% by weight, preferably about 1.0 to about 10% by weight. In an aqueous solution, urea possesses evulsive properties that aid in the penetration and wetting of tissue surfaces. Due to its ability to penetrate tissue surfaces, urea is an ideal evulsing agent for opening up the nail bed to treating bacterial and/or fungal infections (such as onychomycosis and paronychia) associated with fingernails and toenails.

In certain embodiments, the solution may also contain up to about 5.0% by weight of a keratolytic agent to help disrupt the nail surface and to permit the penetration of the active component. Exemplary keratolytic agents that can be employed in practicing the invention include salicylic acid, acetic acid, or glycolic acid, or combinations of these agents.

The lacquer of the invention may also contain a minor amount of an effective solvent (i.e., up to about 4.0% by weight) to aid in the absorption of the desired agents. Exemplary solvents include dimethylsulfoxide and ethyl acetate. However, even those embodiments containing minor amounts of solvents are water based, since the main ingredient of the composition is a water based lacquer.

The solution may also include one or more natural additives suitable for application to the skin, in order to improve the appearance, texture or fragrance of the composition. Exemplary additives include willow bark extract and pau d'arco, an herbal extract, which is added to provide emolliency and a pleasant fragrance.

The water based nail lacquer of the composition of the invention preferably comprises about 93.55% water based lacquer, but can employ between 85 and 95% water based lacquer (by weight). An exemplary water based lacquer is ZMR #19 water based lacquer, from Z.M.R. Corp. of Allendale, N.J. The principal constituents of ZMR #19 lacquer are water, acrylic-urethane copolymer and dipropylene colycolmethyl ether. The water based lacquer provides many advantages over other nail lacquers, particularly organic solvent based nail lacquers. Because the lacquer is water based, the nail lacquer spreads evenly over the nail and surrounding tissues. This is in contrast to nitrocellulose organic solvent based lacquers, which are viscous and difficult to apply and require an organic solvent carrier. Further, because the lacquer is water based, it has the capacity for solubilizing the urea and delivers it more evenly and more efficiently throughout the nail and the surrounding infected areas as compared to organic solvent-based lacquers. This is particularly important in treating fungal infections which are embedded beneath the surface of the nail. The water based lacquer is non-drying and can more easily reach the infected areas beneath the nail than organic solvent based lacquers, where fungal and bacterial infections are the most difficult to treat, allowing application of the antifungal agent directly onto the nail bed.

The composition may also include one or more preservatives suitable for application to the skin, of the type commonly used in the art. An exemplary preservative is Germaben II, a commercially available preservative supplied by Sutton Labs of Chatham, N.J. Germaben II comprises propylene glycol, methylparaben, propylparaben and diazolylidinyl urea.

An exemplary formulation of the topically applied nail lacquer composition of the invention comprises between about 85–95 weight % water based lacquer; 0.5–1.5 weight % Germaben II; 0.5–10.0 weight % urea; 1.0–10.0 weight % deionized water; and 0.1–0.6 weight % natural additives (such as Willow Bark extract and/or pau d'arco). In a particularly preferred embodiment, the composition comprises about 93.55 weight % water based lacquer; about 1.00 weight % Germaben II; about 1.25 weight % urea USP; about 3.70 weight % deionized water; and about 0.5 weight % natural additives. Since the composition is not an organic solvent based lacquer, it does not require the use of solvents, plasticizers, resins and hardeners.

Table I below depicts the percent range of components of typical formulations of the invention.

TABLE 1

ANTIMICROBIAL TOPICAL WATER BASED NAIL LACQUER
(Weight %)

| | BROAD RANGE | Preferred | Especially Preferred |
|---|---|---|---|
| 1) Water Based Nail Lacquer | 85–95 | 90–95 | 93.55 |
| 2) Germaben II | 0.5–1.5 | 0.75–1.25 | 1.00 |
| 3) Urea USP | 0.5–10 | 1.0–10 | 1.25 |
| 4) Deionized water | 1.0–10.0 | 3.0–5.0 | 3.70 |
| 5) Natural additives (e.g. (willow bark extract and Pau D'aco) | 0.1–.6 | 0.2–0.5 | 0.5 |

In other embodiments, the composition may contain up to about 5.0% of an additional keratolytic agent (e.g., salicylic acid, acetic acid or glycolic acid, or combinations thereof), in addition to or instead of urea.

In still other embodiments, the composition may contain up to about 4.0% by weight of a solvent (e.g., dimethylsulfoxide, ethyl acetate).

As stated previously, the nail lacquer of the invention can be used to treat a variety of conditions through nail evulsion to better treat the nail bed for onychomycosis, pedis, paronychia as well as other yeast and/or fungal infections of the nail and skin. The nail lacquer may be provided in the form of a kit, including a brush applicator and a bottle or vial containing the nail lacquer, or in a spray dispenser. The kit may also include a nail scrub liquid and a nail brush. Nail scrub is a nail rejuvenator and cleanser which is applied to the nail surface and then scrubbed briskly with the nail brush. The nail scrub is useful for smoothing out rough, thickened nails and for reducing discoloration from fungus infections. For purposes of storing the nail lacquer of the present invention, the lacquer should preferably be stored at controlled room temperatures between 15°–30° C. (50°–86° F.).

The nail lacquer composition may be applied conventionally to the surface of an infected finger or toenail by depositing a layer of the composition on the surface of the toenail or fingernail. The composition may be applied by any of the methods commonly used to apply topical compositions or creams, such as with an applicator or dispenser such as a brush, sponge, patch, dropper, tubular dispenser or spray. Exemplary spray methods include aerosol spray and conventional non-aerosol pump sprays. The composition may also be applied with a cloth, towel or tissue, such as a facial tissue.

The lacquer composition may be applied evenly, such as by way of the applicator, over the nails and surrounding infected tissues. Once applied, the lacquer should preferably be allowed to stand undisturbed on the nail (in the same manner as conventional nail polishes) until it has dried. The lacquer will form a hardened enamel over the nail after drying. The lacquer will also form a hardened clear enamel over the tissues surrounding the nail. Depending on the amount of enamel applied, it may take approximately between about 5 and 6 minutes for the lacquer to harden. The lacquer should preferably not be layered with one coat on top of the other. The enamel of the present invention, made from the nail lacquer as specified in Table 1, has been shown to form an enamel surface quickly and evenly over the surface of the nail and has proven to be adherent and effective in partially or completely evulsing the nail.

The water based enamel will harden on the nail and seep into the border between the nail and the tissues and to a certain extent will move underneath the nail if applied at the top and side edges of the nail. This is important in partially or completely evulsing the nail, and in treating infections that have manifested themselves underneath the surface of the nail. The lacquer can be applied liberally until all of the infected area is covered by the hardening enamel. The surface of each infected fingernail and toenail should be covered with the nail lacquer in order to help treat the underlying infection by opening up the nail bed for better application of the active agent directly on the nail bed. The lacquer can be reapplied if the enamel is removed (e.g. by bathing or washing) from a nail surface.

For effective treatment, the lacquer should preferably be applied once each day, preferably in the morning. After wearing the enamel for a full day, the enamel should be completely removed before adding another coat. The enamel can be removed by most non acetone-free nail polish removers. The fact that the enamel is water based significantly facilitates removal of the lacquer in comparison to organic solvent based nail lacquers. The lacquer should be applied daily as treatment requires but no longer than a month unless directed by a podiatrist or physician.

As stated previously, fungal and bacterial infections that spread beneath the surface of the nail in the nail bed are particularly difficult to treat. While the water based lacquer does serve as an improved delivery system to the nail over conventional organic solvent based nail lacquers, it ordinarily does not penetrate deeply beneath the surface of the nail in the nail bed between the nail and the tissue. This is a particularly difficult area to reach. However, the urea component of the nail lacquer serves to soften the nail, thereby increasing the permeability of the nail so that an antimicrobial agent may reach beneath the nail and the nail bed. Thus, when the nail lacquer is applied, the nail is partly or completely evulsed. Subsequently, antimicrobial and antiviral agents are able to move to some degree into the nail bed to successfully treat any fungal or microbial infections that have manifested there. Ultimately, the composition of the invention causes evulsion of the nail, thereby permitting clear access to the nail bed by antimicrobial or antiviral agents.

The keratolytic agents will aid in disruption of the nail matrix to allow for the penetration of the desired agent.

After the nail lacquer is applied, the lacquer may be allowed to slowly harden, forming a suitable film over the nail and a hardened enamel. There are no film forming agents required or any synthetic resins required (except that which is in the water based lacquer) for forming the enamel, which has dermatological benefits in that synthetic resins are often associated with allergic responses.

The present invention is described in the following working example without limiting the scope thereof. Unless otherwise indicated, all parts and percentages are on a weight basis.

EXAMPLE

| Compound | Weight % |
|---|---|
| MR #19 Water Based Lacquer | 93.55 |
| Germaben II | 1.00 |
| Urea USP | 1.25 |
| Deionized Water | 3.70 |
| Willow Bark Extract | .25 |
| Pau D'arco | .25 |

A water based urea nail lacquer of the present invention may be prepared as follows. Water and urea are mixed and warmed slightly to dissolve the urea. The solution is then added to the base material, consisting of a water based nail lacquer. Germaben II is thereafter admixed with the base material and the resulting composition is mixed further. Willow bark extract and Pau D'arco is added and the resulting composition is mixed. The solution is stored in an airtight container at room temperature.

The solution is then applied to the surface of a toe nail infected with paronychia.

In those embodiments containing an additional keratolytic agent, the keratolytic agent is mixed with the water and urea. Similarly, in those embodiments in which minor amounts of a solvent (up to about 4.0% by weight) are included, the solvent may be added to the base material comprising the water based lacquer, prior to admixture with the water and urea.

It may be therefore seen that an improved urea nail lacquer is provided which is particularly effective in helping to treat fungal and bacterial infections of the nail and nail bed.

I claim:

1. A topical nail enamel composition comprising
   (a) from about 85 to about 95% by weight water based nail lacquer;
   (b) from about 0.5 to about 1.5% by weight of a preservative;
   (c) from about 0.5 to about 10% by weight urea;
   (d) from about 1.0 to about 10% by weight deionized water; and
   (e) from about 0.1 to about 0.6% by weight of a natural additive.

2. The topical nail enamel composition of claim 1, further comprising up to about 5.0% by weight of a keratolytic agent.

3. The topical nail enamel composition of claim 2, wherein said keratolytic agent is selected from the group consisting of salicyclic acid, acetic acid, glycolic acid, and combinations thereof.

4. The topical nail enamel composition of claim 1, further comprising up to about 4.0% by weight of a solvent.

5. The topical nail enamel composition of claim 1 wherein said water based nail lacquer comprises an acrylic-urethane copolymer.

6. The topical nail enamel composition of claim 1 wherein said preservative comprises propylene glycol, methylparaben, propylparaben and diazolylidinyl urea.

7. The topical nail enamel composition of claim 1 wherein said natural additive is an herbal extract.

8. The topical nail enamel composition of claim 1 comprising about 1.25% by weight urea.

9. The topical nail enamel composition of claim 1 comprising from about 90 to about 95% by weight water based nail lacquer; from about 0.75 to about 1.25% by weight of a preservative; from about 1.0 to about 10.0% by weight urea; from about 3.0 to about 5.0% by weight deionized water; and from about 0.2 to about 0.5% by weight of a natural additive.

10. The topical nail enamel composition of claim 9 comprising about 93.55% by weight of said water based nail lacquer; about 1.0% by weight of a preservative; about 1.25% by weight of urea; about 3.70% by weight deionized water; and about 0.5% by weight natural additives.

11. The topical nail enamel composition of claim 2, wherein said keratolytic agent is salicylic acid.

12. A method of evulsing a toenail or fingernail of a mammal in need thereof, said method comprising topically applying the topical nail enamel composition of claim 1 to the toenail or fingernail of said mammal.

13. A method of treating a bacterial or fungal infection on or under a toenail or fingernail of a mammal, said method comprising the steps of
   (a) evulsing said toenail or fingernail in whole or in part by administering to said toenail or fingernail a composition comprising:
      (i) from about 85 to about 95 weight % water based nail lacquer;
      (ii) from about 0.5 to about 1.5% preservative;
      (iii) from about 0.5 to about 10% by weight urea;
      (iv) from about 1.0 to about 10% by weight deionized water; and
      (v) from about 0.1 to about 0.6% by weight natural additive; and
   (b) administering an antibacterial or antifungal agent on or under said toenail or fingernail.

14. The method of claim 13 wherein said step of administering said composition comprises applying a layer of said composition on the surface of said toenail or fingernail.

15. The method of claim 13 wherein said step of applying said composition comprises depositing said composition on the surface of said toenail or fingernail with a brush, sponge, patch, tubular dispenser, dropper, cloth, tissue or spray.

16. The method of claim 13, said composition further comprising up to about 5.0% by weight of a keratolytic agent.

17. The method of claim 13, said composition further comprising up to about 4.0% by weight of a solvent.

18. A method of treating a bacterial or fungal infection on or under a toenail or fingernail of a mammal, said method comprising the steps of
   (a) evulsing said toenail or fingernail in whole or in part by administering to said toenail or fingernail a composition comprising:
      (i) from about 85 to about 95 weight % water based nail lacquer;
      (ii) from about 0.5 to about 10% by weight urea;
      (iii) from about 1.0 to about 10% by weight deionized water; and
   (b) administering an antibacterial or antifungal agent on or under said toenail or fingernail.

19. The method of claim 18, said composition further comprising up to about 5.0% by weight of a keratolytic agent.

20. The method of claim 18, said composition further comprising from up to about 4.0% by weight of a solvent.

* * * * *